United States Patent [19]

HaKansson et al.

[11] Patent Number: 5,149,873
[45] Date of Patent: Sep. 22, 1992

[54] PROCESS FOR THE PURIFICATION OF MANDELIC ACID N,N-DIETHYLAMIDE

[75] Inventors: Christer L. HaKansson, Vikingsgatan; Bengt L. Karlsson, Stenbocksgatan, both of Sweden

[73] Assignee: Rexolin Chemicals AB, Helsingborg, Sweden

[21] Appl. No.: 649,401

[22] Filed: Feb. 1, 1991

[51] Int. Cl.$^5$ .................. C07C 235/34; C07C 231/24
[52] U.S. Cl. ..................................................... 564/170
[58] Field of Search ......................................... 564/170

[56] References Cited

U.S. PATENT DOCUMENTS 3,876,800  4/1975  Krausz et al. ...................... 514/570
4,192,892  3/1980  Thorsell et al. .................... 564/170

FOREIGN PATENT DOCUMENTS 2714671  10/1977  Fed. Rep. of Germany.

Primary Examiner—Carolyn Elmore
Attorney, Agent, or Firm—William L. Baker; Kevin S. Lemack

[57] ABSTRACT

A process for the purification of mandelic acid N,N-diethylamide, DEM, by forming a crystalline adduct of DEM with a calcium halide and water.

9 Claims, No Drawings

PROCESS FOR THE PURIFICATION OF MANDELIC ACID N,N-DIETHYLAMIDE

The present invention relates to a process for the purification of mandelic acid N,N-diethylamide, abbreviated DEM herein. This compound

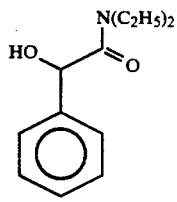

and related mandelamides are useful as insect repellents as described in the Swedish Patent 409808 (1979) to W. Thorsell et al.

The synthesis of DEM can be performed by a 4-step route such as described in the above Swedish patent. Whatever the method of synthesis it is important that the crude DEM obtained is upgraded to obtain a purified material suitable for application to the skin.

The purification of DEM is difficult due to:
a) the very high boiling point and the poor thermal stability, which combine to make fractional distillation very difficult on an industrial scale;
b) the low melting point of DEM, 27°–30° C., and the high viscosity, which make it difficult to crystallize DEM.

It is therefore an object of the present invention to provide a process whereby DEM can be purified in a practical way on an industrial scale using ordinary standard equipment.

The essence of the present invention lies in the surprising discovery that DEM forms crystalline, high-melting adducts with calcium halides and water. Preferred halides are selected from chloride and bromide, and embodiments wherein the halide is chloride are particularly preferred.

More specifically, we particularly prefer two different adducts with the compositions $DEM \cdot CaCl_2 \cdot 2H_2O$ and $DEM \cdot CaCl_2 \cdot 6H_2O$, respectively.

Any of such adducts of DEM with calcium halides and water can be used in the purification of DEM by crystallization.

The novel adducts according to the invention are stable in the presence of sufficiently hydrophobic non-polar or moderately polar solvents such as hydrocarbons, ethers and esters. Solvents of these types are therefore useful crystallization media and will serve to dissolve the impurities that are to be removed.

Although the present invention covers any adducts with calcium halides and water the invention will be illustrated in the following mainly with reference to adducts with calcium chloride and water.

The crystallization of DEM as the adduct with $2H_2O$ can be performed by stirring the calculated amount of $CaCl_2 \cdot 2H_2O$ with a solution of DEM in a solvent. The $CaCl_2 \cdot 2H_2O$ will dissolve due to adduct formation and $DEM \cdot CaCl_2 \cdot 2H_2O$ will then crystallize rapidly from the solution.

In a modified procedure a hydrophilic solvent such as water or a lower alcohol is added to redissolve the $DEM \cdot CaCl_2 \cdot 2H_2O$ or to prevent it from precipitating too rapidly. The crystallization may then be completed by distilling off the hydrophilic solvent.

The adduct with $6H_2O$ can be crystallized by contacting a solution of DEM in a sufficiently hydrophobic solvent with an approximately 50% aqueous solution of $CaCl_2$, corresponding to $CaCl_2 \cdot 6H_2O$. When the two essentially immiscible solutions are stirred together, crystals of $DEM \cdot CaCl_2 \cdot 6H_2O$ will start forming. The process is typically performed at room temperature and the crystallization takes place at a convenient rate if moderate stirring is applied. A high yield of good crystals can thus be obtained in as little as one half hour, although stirring is preferably continued for one or a few hours.

The crystals of $DEM \cdot CaCl_2 \cdot 2H_2O$ or $DEM \cdot CaCl_2 \cdot 6H_2O$ thus obtained are typically almost colourless. They are separated from the coloured mother liquor by filtration or centrifugation and washed with solvent. Purified DEM is then set free by stirring the crystals, normally in the presence of adhering solvent, with a suitable amount of water. DEM, together with any solvent, is obtained as an oil phase that separates from the aqueous phase containing the calcium chloride.

After collecting the DEM phase any traces of calcium chloride are removed by extracting with water. Evaporation of solvent leaves DEM of high purity.

The present invention will now be further exemplified by non-limiting examples.

EXAMPLE 1

Preparation of $DEM \cdot CaCl_2 \cdot 2H_2O$ adduct

DEM (41 g=0.2 mol) was dissolved in toluene (163 ml). While stirring at 45° C., finely crystalline $CaCl_2 \cdot 2H_2O$ (22.1 g=0.2 mole) was added. The calcium chloride dissolved rapidly but before dissolution was complete a new precipitate started to form. After stirring for 15 minutes this was filtered off with suction. 64 g of moist crystals were obtained.

EXAMPLE 2

Preparation of adduct with recrystallization

A slurry of adduct in toluene was prepared as in Example 1. Ethanol (88 ml) was added and the temperature was raised to about 90° C. to dissolve the crystals. The ethanol was then slowly distilled off, whereby the adduct crystallized in a purified form.

EXAMPLE 3

Preparation of $DEM \cdot CaCl_2 \cdot 6H_2O$

The formation of this adduct was demonstrated with crude DEM of 95% purity:

Crude DEM (50 g=0.229 mol) was dissolved in ethyl acetate (116 ml). $CaCl_2 \cdot 2H_2O$ (32.0 g=0.217 mol) was dissolved in water (15.7 g=0.870 mol) at 40° C. The two, essentially immiscible solutions were stirred together. After about 15 minutes crystals started to form in the aqueous phase and after another 15 minutes the crystallization was complete. The resulting slurry of crystals in ethyl acetate was filtered to give 79 g of almost colourless adduct.

EXAMPLE 4

Preparation of $DEM \cdot CaCl_2 \cdot 6H_2O$

The process of Example 3 was repeated but with toluene, butyl acetate or isobutyl acetate instead of ethyl acetate. All these three solvents gave a yield of about 85 g of almost colourless adduct.

EXAMPLE 5

Recovery of Purified DEM by Hydrolysis of DEM·CaCl$_2$·6H$_2$O 10.0 g of the adduct from Example 3 was stirred with 10.0 g water for 15 minutes at 30° C. The lower phase, containing calcium chloride in water, was then separated from the organic phase. The latter was washed with water to give 4 g of DEM as an almost colourless oil.

EXAMPLE 6

Recovery of Purified DEM by Hydrolysis of DEM·CaCl$_2$·6H$_2$O 10.0 g of the adduct from Example 3 was stirred with 5.0 g water and 5 g ethyl acetate. After stirring for 15 minutes at 30° C., the lower phase, consisting of a 25% solution of calcium chloride in water, was separated from the organic phase. The latter was washed with water and evaporated to give 4.5 g of DEM as an almost colourless oil that crystallized on standing.

EXAMPLE 7

Preparation of DEM·CaBr$_2$·2H$_2$O adduct

In a beaker with stirring there was charged in the order given:

DEM 10.62 g=0.0513 mol
Toluene 50 ml
CaBr$_2$·H$_2$O 11.68 g=0.0513 mol CaBr$_2$ and 0.076 mol H$_2$O (11.7% water)
Water 0.42 g=0.023 mol On heating to 65°–70° C. the calcium bromide dissolved. Before dissolution was complete a new precipitate of DEM·CaBr$_2$·2H$_2$O was formed.

This precipitate was filtered off and was found to dissolve in water with liberation of DEM as an oily phase.

We claim:

1. A process for the purification of mandelic acid N,N-diethylamide, DEM, by forming a crystalline adduct of DEM with a calcium halide and water.

2. A process according to claim 1, wherein the halide is selected from chloride and bromide.

3. A process according to claim 2, wherein the halide is chloride.

4. A process according to claim 3, wherein the adduct is DEM·CaCl$_2$·2H$_2$O.

5. A process according to claim 3, wherein the adduct is DEM·CaCl$_2$·6H$_2$O.

6. A process according to claim 4, wherein the crystalline adduct is obtained from a solution of DEM in a hydrophobic solvent by stirring with CaCl$_2$·2H$_2$O.

7. A process according to claim 6, wherein the crystallization is modified by the addition of a hydrophilic solvent.

8. A process according to claim 5, wherein the crystalline adduct DEM·CaCl$_2$·6H$_2$O is obtained by stirring a solution of DEM in an organic solvent or mixture of solvents with an approximately 50% aqueous solution of calcium chloride.

9. A process according to any preceding claim, comprising the further steps of separating crystalline adduct and contacting same with water to liberate the purified DEM.

* * * * *